(12) United States Patent
Supamahitorn et al.

(10) Patent No.: US 11,793,875 B2
(45) Date of Patent: *Oct. 24, 2023

(54) HIGH LOAD DISPERSIONS

(71) Applicant: Austin Research Labs Corp., Buffalo, NY (US)

(72) Inventors: Jai Supamahitorn, Buffalo, NY (US); Lauren McMillan, Hamburg, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/745,937

(22) Filed: May 17, 2022

(65) Prior Publication Data

US 2022/0347301 A1 Nov. 3, 2022

Related U.S. Application Data

(60) Continuation of application No. 16/928,227, filed on Jul. 14, 2020, now Pat. No. 11,331,389, which is a
(Continued)

(51) Int. Cl.
| | | |
|---|---|---|
| *A61K 47/02* | (2006.01) | |
| *A61K 47/52* | (2017.01) | |
| *A01N 25/04* | (2006.01) | |
| *A01N 39/00* | (2006.01) | |
| *A01N 33/12* | (2006.01) | |
| *A61K 9/10* | (2006.01) | |
| *A61K 31/14* | (2006.01) | |
| *A61K 45/06* | (2006.01) | |
| *A61K 31/167* | (2006.01) | |

(52) U.S. Cl.
CPC ............ *A61K 47/02* (2013.01); *A01N 25/04* (2013.01); *A01N 33/12* (2013.01); *A01N 39/00* (2013.01); *A61K 9/10* (2013.01); *A61K 31/14* (2013.01); *A61K 31/167* (2013.01); *A61K 45/06* (2013.01); *A61K 47/52* (2017.08); *Y02A 50/30* (2018.01)

(58) Field of Classification Search
CPC .. A01N 25/04; A61K 47/48015; A61K 47/02; A61K 45/06
See application file for complete search history.

(56) References Cited

U.S. PATENT DOCUMENTS 2,965,687 A 12/1960 Loten et al.
3,061,512 A 10/1962 Anderson et al.
(Continued)

FOREIGN PATENT DOCUMENTS

EP 0070702 A2 1/1983
EP 0265101 A2 4/1988
(Continued)

OTHER PUBLICATIONS

Dyer et al., "Testing a new alcohol-free hand sanitizer to combat infection." Aorn J. Aug. 1998; 68(2):239-41, 243-4, 247-51.
(Continued)

*Primary Examiner* — Jianfeng Song
(74) *Attorney, Agent, or Firm* — CASIMIR JONES, S.C.; Tanya A. Arenson

(57) ABSTRACT

The present invention relates to the field of carrier and delivery systems for active molecular compounds. In particular, the present invention provides aqueous dispersions for delivery of active molecular compounds.

12 Claims, 5 Drawing Sheets

Related U.S. Application Data continuation of application No. 16/363,649, filed on Mar. 25, 2019, now Pat. No. 10,709,785, which is a continuation of application No. 15/688,241, filed on Aug. 28, 2017, now Pat. No. 10,238,744, which is a continuation of application No. 14/854,925, filed on Sep. 15, 2015, now Pat. No. 9,744,238, which is a continuation of application No. 14/492,890, filed on Sep. 22, 2014, now Pat. No. 9,131,684, which is a division of application No. 13/350,532, filed on Jan. 13, 2012, now Pat. No. 8,858,970.

(60) Provisional application No. 61/432,381, filed on Jan. 13, 2011.

(56) References Cited

U.S. PATENT DOCUMENTS

| | | |
|---|---|---|
| 4,365,030 A | 12/1982 | Oswald et al. |
| 4,474,705 A | 10/1984 | Hughie et al. |
| 4,474,706 A | 10/1984 | Hughie et al. |
| 4,849,006 A | 7/1989 | Knudson |
| 5,145,596 A | 9/1992 | Blank et al. |
| 5,686,088 A | 11/1997 | Mitra et al. |
| 6,015,816 A | 1/2000 | Kostyniak |
| 6,261,997 B1 | 7/2001 | Rubin et al. |
| 6,288,076 B1 * | 9/2001 | Kostyniak ............ A61K 31/327 514/299 |
| 7,049,339 B2 | 5/2006 | Thomson |
| 8,858,970 B2 | 10/2014 | Supamahitorn et al. |
| 9,131,684 B2 | 9/2015 | Supamahitorn et al. |
| 9,744,238 B2 | 8/2017 | Supamahitorn et al. |
| 10,238,744 B2 | 3/2019 | Supamahitorn et al. |
| 2002/0086039 A1 | 7/2002 | Lee et al. |
| 2002/0120242 A1 | 8/2002 | Tyrrell et al. |
| 2003/0161866 A1 | 8/2003 | Kostyniak |
| 2004/0241206 A1 | 12/2004 | Ketelson |
| 2006/0128585 A1 | 6/2006 | Adair |
| 2006/0223889 A1 | 10/2006 | Embrechts et al. |
| 2006/0246149 A1 | 11/2006 | Buchholz et al. |
| 2012/0183588 A1 | 7/2012 | Supamahitorn et al. |
| 2015/0011641 A1 | 1/2015 | Supamahitorn et al. |
| 2016/0000920 A1 | 1/2016 | Supamahitorn et al. |
| 2017/0354733 A1 | 12/2017 | Supamahitorn et al. |

FOREIGN PATENT DOCUMENTS

| | | | |
|---|---|---|---|
| EP | | 0775686 A1 | 5/1997 |
| WO | WO | 199731709 A1 | 9/1997 |
| WO | WO | 199731873 A1 | 9/1997 |
| WO | WO | 2003059193 A2 | 7/2003 |
| WO | WO | 2008076807 A2 | 6/2008 |
| WO | WO | 2012097302 A1 | 7/2012 |

OTHER PUBLICATIONS

Estevez et al., "Spectroscopic study of the adsorption of rhodamine 6g on laponite b for low loadings." Clay Minerals, Jan. 1, 1994, 29:105-113.

Evans J., "Organic Waste Treatment with Organically Modified Clays." EPA/600/9-89/072, Proceedings of the 3rd International Conference on New Frontiers for Hazardous Waste Management, Sep. 10-13, 1989, pp. 48-58.

G Lagaly: "Bentonites: adsorbents of toxic substances", Progress in Colloid & Polymer Science, Jan. 1, 1994 (Jan. 1, 1994), pp. 61-72.

Healy B., "Surface Modified Clays: An Innovative Technology for Groundwater Remediation." Ground Water Management, Jan. 1, 1993, pp. 61-69.

Marples, "A laboratory model for the investigation of contact transfer of micro-organisms." J Hyg (Lond). Apr. 1979;82(2):237-48.

\* cited by examiner

PTA 5    0.13% Benzalkonium chloride in formulation
PTA 7    0.13% "Bound" Benzalkonium chloride in formulation

HIGH LOAD DISPERSIONS

CROSS-REFERENCE TO RELATED APPLICATION

The present invention is a continuation of U.S. patent application Ser. No. 16/928,227 filed Jul. 14, 2020, now U.S. Pat. No. 11,331,389, issued May 17, 2022, which is a continuation of U.S. patent application Ser. No. 16/363,649 filed Mar. 25, 2019, now U.S. Pat. No. 10,709,785, issued Jul. 14, 2020, which is a continuation of U.S. patent application Ser. No. 15/688,241 filed Aug. 28, 2017, now U.S. Pat. No. 10,238,744, issued Mar. 26, 2019, which is a continuation of U.S. patent application Ser. No. 14/854,925 filed Sep. 15, 2015, now U.S. Pat. No. 9,744,238, issued Aug. 29, 2017, which is a continuation application of U.S. patent application Ser. No. 14/492,890 filed Sep. 22, 2014, now U.S. Pat. No. 9,131,684, issued Sep. 15, 2015, which is a divisional application of U.S. patent application Ser. No. 13/350,532 filed Jan. 13, 2012, now U.S. Pat. No. 8,858,970, issued Oct. 14, 2014, which claims priority to U.S. Provisional Patent Application Ser. No. 61/432,381 filed Jan. 13, 2011, each of which are herein incorporated by reference in its entirety.

FIELD OF THE INVENTION

The present invention relates to the field of carrier and delivery systems for active molecular compounds. In particular, the present invention provides aqueous dispersions for delivery of active molecular compounds.

BACKGROUND OF THE INVENTION

Current delivery systems for various biologically active compounds do not provide prolonged effects without high doses or frequent reapplication. In addition, topical application of such compounds frequently results in side effects such as irritation or toxicity. The irritation in many cases can rise to the level of pain, e.g., in the case of application of free halogens or alcohols. In addition, carrier systems themselves can create undesirable side effects.

As an example, hand antiseptic agents are designed to remove most transient flora just as plain soaps and detergents do, but they are unable to exert either a persistent or a residual antimicrobial activity on remaining flora. This contributes to making hospital environments very dangerous, especially to patients, because there are no products in general use on the market that allow for both immediate and sustained kill of microbes required to prevent hospital acquired infections. Currently, only superficial cleaning is provided and this is not good enough for the healthcare environment. In part, as a result of this superficial cleaning, it is believed that as many as 100,000 people die each year from hospital acquired infections. There is a danger of infection for every patient that enters a hospital, especially those bound for surgery, because there are currently insufficient reliable means of removing, reducing, and maintaining the reduction of pathogens on the hands of nurses, doctors and surgeons to a degree necessary to entirely prevent infection. Currently accepted methods/standards only require hand hygiene products to achieve a 2-3 log reduction in vivo in order to enter the professional care/healthcare market without considering extended antimicrobial effects. Failure to consider extended effects is at odds with the fact that hospital patients are already not well and generally have depressed immune systems which put them at high risk for infection, and are therefore the population most in need of an effective/reliable pathogen killer.

Alcohol-based hand sanitizers, so far, have been the preferred agents for hygienic, so-called "waterless" hand-disinfection hand-rubs because they seem to offer more convenience than aqueous solutions and because they purport to offer an optimal antimicrobial spectrum (that is, they are active against all bacteria and most clinically important viruses, yeasts, and fungi); no wash basin is necessary for their use, and they can be readily available at bedsides. It has been shown that alcohol-based preparations in general have more rapid action than products containing other antiseptics (e.g., chlorhexidine gluconate or providone iodine), require less time than traditional hand washing, and contribute to decreased infection rates. Furthermore, they are not likely to microbially contaminate health-care workers' clothing; and exhibit rapid action.

However, alcohol-based hand washes have several drawbacks. For one, in some cases frequent hand-washing even with alcohol, may not result in the desired microbial reduction. For example, after performing a vaginal examination, it is recommended to disinfect hands in a chlorinated solution. More importantly, alcohol-based hand sanitizers stop working the instant they dry. That is, as soon as the alcohol evaporates, its anti-microbial activity ceases. In addition, alcohol washes do not exhibit persistence in their antimicrobial activity. Although the leading manufacturer of alcohol-based hand sanitizers claims that their product kills 99.99% of most common microorganisms in as little as 15 seconds, the alcohol-based hand sanitizers dry in 8-10 seconds and fall below the efficacious concentration of alcohol in seconds. Recontamination occurs as soon as the hands come into contact with a contaminated surface. Moreover, recontamination is also likely to occur even before the hands come into contact with a contaminated surface. It is now known that contamination can occur by contact with microbes that are in the room atmosphere.

It has been reported that alcohol-based hand sanitizers offer no residual protection, and that if a user's hands feel dry after rubbing them together for 15 seconds, an insufficient volume of sanitizer was likely applied (e.g., *A laboratory model for the investigation of contact transfer of microorganisms*, Marples, R. R. & Towers, A. G. The Journal of Hygiene, 82(2), 237-248 (1979); herein incorporated by reference in its entirety). Moreover, gelled alcohol-based hand sanitizers became less effective with repeated use and made the skin dirtier, not cleaner due to removal of protective natural skin oils and entrapment of dead skin cells by the polymer thickeners used in the gelled alcohol-based products. In a referenced study to simulate repeated usage, subject's alcohol-based sanitized hands were repeatedly inoculated with bacteria followed by an application of hand sanitizer, then evaluated for antimicrobial effectiveness. The antimicrobial efficacy of the alcohol-based hand sanitizer showed a markedly decreased antimicrobial efficacy with subsequent contamination and decontamination cycles. In addition to these objective results, subjects were asked to subjectively evaluate the condition of their hands after the completion of the test protocol. 47% of the subjects who had completed the test protocol with the alcohol-based hand sanitizer reported palmar pain or discomfort, and tended to indicate some discomfort in palmar surfaces for one to several days after the test. (e.g., *Testing a new, alcohol-free sanitizer to combat infection*, Dyer, D. L., Gerenraich, K. B., & Wadhams, P. S., Association of Operating Room Nurses Journal, 68(2), 239-251 (1998); herein incorporated by reference in its entirety).

Thus, in a manner similar to other topically applied active compounds, the desired effects of the active ingredient does not last.

An additional problem with alcohol-based hand wash preparations is the fact that alcohol-based hand wash preparations tend to strip the skin of essential oils and sebum, which is a further undesirable side effect. Moreover, when they are applied to wounds not only do alcohol-based hand wash preparations increase the risk of injury to the tissue of the wound and cause pain, they also form a coagulum under which bacteria may subsequently thrive (e.g., *Testing a New Alcohol-Free Hand Sanitized to Combat Infection*, Dyer, D. D., Gerenraich, K. B., and Wadhams, P. S., AORN Journal, Vol. 68, No. 2, Pages 239-251 (1998); herein incorporated by reference in its entirety).

Wearing gloves to prevent re-infection of hands presents similar problems in compliance with hand hygiene. Gloves may be thought of as adding another layer of skin to one's hands, but failure to thoroughly wash gloved hands, remove, or change gloves after each patient or other contaminating contact, results in the same germ transfer problem. Moreover, it is known that many potential glove wearers are allergic to the gloves or the powders used with the gloves.

It can be seen there is a problem in the field in that while many active compounds can be effective, the effectiveness may be transient, e.g., the immediate effectiveness of many of the presently available hand-sanitizers, including soap, detergents, and antiseptic agents, as well as the alcohol washes discussed above, may be acceptable at the time of washing, their effectiveness quickly diminishes in a short time after washing, frequently measured in seconds.

Similar problems, e.g., with sustained effectiveness and side effects arise in other types of dispersions for topical use, e.g., topical analgesics, anti-inflammatories, antihistamines, colorant, keratolytics, etc. and perhaps even for oral use, e.g., a clay loaded with an anti-diarrheal compound, purgative, antacid or antibiotic.

A number of patents address the possibility of causing an antimicrobial compound bound to a substrate to be suspended in water. Specific patents are U.S. Pat. Nos. 6,015,816; 6,288,076; and U.S. Patent Publication 2003/0161866A1; herein incorporated by reference in their entireties. U.S. Patent publication 2003/0161866 recognizes that suspensions in water of ion exchange materials such as clays may be combined with certain ligands. Suspensions as describe in these patent publications are generally of very low viscosity and the publication does not seem to recognize that the compositions they describe simply seem to run from surfaces to which they are applied. While this may be acceptable in non-topical applications where the application can be quickly dried at high temperature, such would not be acceptable in topical applications where skin may not be exposed to sufficiently high temperatures for quick drying. Thus none of the above approaches provide sufficient benefit.

SUMMARY OF THE INVENTION

In some embodiments, provided herein are methods for the preparation and use of a dispersion that permits high loading of active ingredients that permit the active ingredients to provide both immediate and long lasting effects.

Also provided herein are formulations and formulation methods comprising disinfecting solution that allows for a slow release of an active disinfecting component over time.

Further provided herein are compositions that reduce toxicity, irritation and side effects of included active ingredients.

Further provided herein are formulations that adhere to a biological surface, e.g., skin, for an extended period of time and reduces the spread of infection.

Further provided herein are disinfecting compositions that include a skin moisturizing component, a humectant component and/or a thickening component.

In some embodiments, the present invention provides a composition comprising a dispersion having: (a) a continuous phase, wherein the continuous phase is an aqueous liquid or gel; and (b) a dispersed phase comprising: (i) a hydrophilic submicron particle substrate having electrically charged binding sites; (ii) an intermediate component comprising a first hydrophobic moiety and an ionic moiety, wherein the ionic moiety is attracted to the electrically charged binding sites; and (iii) an active agent comprising a second hydrophobic moiety attracted to the first hydrophobic moiety. In some embodiments, the dispersed phase comprises a particulate material suspended within the continuous phase. In some embodiments, dispersions further comprise (c) at least one of a humectant, emollient, detackifier, moisturizer, thickener, or chelating agent suspended or dissolved in the continuous phase. In some embodiments, the dispersion is configured for topical administration to a subject. In some embodiments, the continuous aqueous phase comprises an epidermally compatible humectants, an epidermally compatible thickener, or both. In some embodiments, the hydrophilic submicron particle substrate comprises a hydrophilic clay. In some embodiments, the hydrophilic clay comprises one or more of smectite, laponite and bentonite clays. In some embodiments, the hydrophilic clay comprises laponite. In some embodiments, the intermediate component comprises a quaternary ammonium compound. In some embodiments, the quaternary ammonium compound comprises benzethonium chloride or derivatives thereof. In some embodiments, the active agent comprises one or more of: an antimicrobial, an analgesic, an antifungal, an insect repellent, an antiperspirant, and an anti-inflammatory. In some embodiments, the active agent comprises an antimicrobial. In some embodiments, the dispersion comprises a chelating agent. In some embodiments, the chelating agent is a gluconate. In some embodiments, the dispersion comprises an emulsifier. In some embodiments, the emulsifier is chosen from a group comprising cetyl alcohol and nonionic emulsifying waxes. In some embodiments, the dispersion comprises a humectant. In some embodiments, the humectant is chosen from a group comprising glycerol, propylene glycol, liquid silicone, and mixtures thereof. In some embodiments, the dispersion comprises a moisturizer. In some embodiments, the moisturizer is selected from the group comprising combined gluconolactone and sodium benzoate, glycerine, and olive oil. In some embodiments, the dispersion comprises a detackifier. In some embodiments, the detackifier is silicone fluid. In some embodiments, the dispersion comprises an emollient. In some embodiments, the emollient is pentaerythrityl tetracaprylate. In some embodiments, the dispersion comprises a thickener. In some embodiments, the thickener is a gelling agent. In some embodiments, the gelling agent is gelatin or collagen. In some embodiments, the dispersion comprises a primary layer, an intermediate layer, and a tertiary layer, wherein the primary layer comprises the hydrophilic submicron particles, wherein the tertiary layer comprises the active agent, and wherein sad intermediate layer comprises the intermediate agent linking the primary layer and the tertiary layer.

In some embodiments, the present invention provides a method of making a dispersion as described above, comprising the steps of: (a) combining hydrophilic submicron particles with an intermediate component to obtain an intermediate blend, wherein the combining is performed in the absence of complete drying; (b) suspending the intermediate blend in the continuous phase to obtain a dispersion of particles in the continuous aqueous phase, wherein the ionic moiety of the intermediate component interacts with the electrically charged binding sites of the hydrophilic submicron particles, and wherein the first hydrophobic moiety is displayed on the surface of the particles; and (c) adding the active agent, wherein the second hydrophobic moiety interacts with the first hydrophobic moiety, thereby linking the active agent to the hydrophilic submicron particles through the intermediate component. In some embodiments, the continuous phase comprises water and at least one of a moisturizer, humectant, a chelating agent and a thickener.

In some embodiments, the present invention comprises a method of making an antimicrobial carrier system comprising the steps of: (a) adding at least one of a moisturizer or humectant to water to form an aqueous suspension; (b) mixing a hydrophilic clay and a quaternary compound to produce a clay and quaternary compound mixture; (c) adding water to the clay and quaternary compound mixture to form a hydrophilic clay-quaternary ammonium compound combination; (d) combining the aqueous suspension and the hydrophilic clay-quaternary ammonium compound combination to obtain a suspension; (e) heating the suspension; (f) dispersing at least one of a gelling agent, a skin adherent, a humectant, a detackifier, a nonaqueous moisturizer, an anti-inflammatory, an emollient, and an emulsifier to obtain a dispersion; (g) heating the dispersion; (h) mixing the dispersion with the suspension; and (i) homogenizing the resulting composition. In some embodiments, the heating steps are performed between 70 and 90° C. In some embodiments, methods further comprise adjusting the pH of the resulting composition between about 5.2 to about 6.2.

In some embodiments, the present invention provides a method of making a carrier system for an active agent, wherein the active agent comprises a cationic moiety and a hydrophobic moiety, comprising: (a) mixing the active agent and a hydrophilic submicron particle substrate to form an active agent-particle mixture; (b) suspending the active agent-particle mixture in an aqueous liquid to form a suspension; and (c) incorporating the suspension into a carrier comprising at least one of a gelling agent, a skin adherent, a humectant, a detackifier, a moisturizer, an anti-inflammatory, an emollient, and an emulsifier. In some embodiments, the method further comprises adjusting the pH of the carrier system to between about 5.2 to about 6.2.

In some embodiments, the present invention provides a method for disinfecting a surface comprising contacting the surface with a dispersion comprising an antimicrobial compound. In some embodiments, the surface is an epidermal surface.

In some embodiments, the present invention provides a method of applying a medicament to an epidermal surface comprising applying a dispersion comprising a medicament.

In some embodiments, a method of the present invention further provides compositions made by any of the manufacturing methods described herein. In some embodiments, the present invention provides manufacturing methods for any of the compositions described herein.

In further embodiments, the present invention provides methods for disinfecting a surface (e.g., skin, wound, mucosal tissue, etc.) including the step of contacting the surface with the above described composition wherein the tertiary layer contains an antimicrobial compound.

In some embodiments, the invention provides for the use of any of the compositions described herein for the treatment of a surface (e.g., topical treatment of subjects). In some embodiments, the invention provides for the use of any of the compounds for the preparation of a medicament for treating a disease or condition (e.g., a disease or condition caused by a bacteria, virus, or fungi).

In some embodiments, the present invention provides the use of dispersion of the present invention in the preparation of a medicament for treating one or more conditions including, but not limited to: acne, infection, wound infection, etc.

DEFINITIONS

Figure 1:
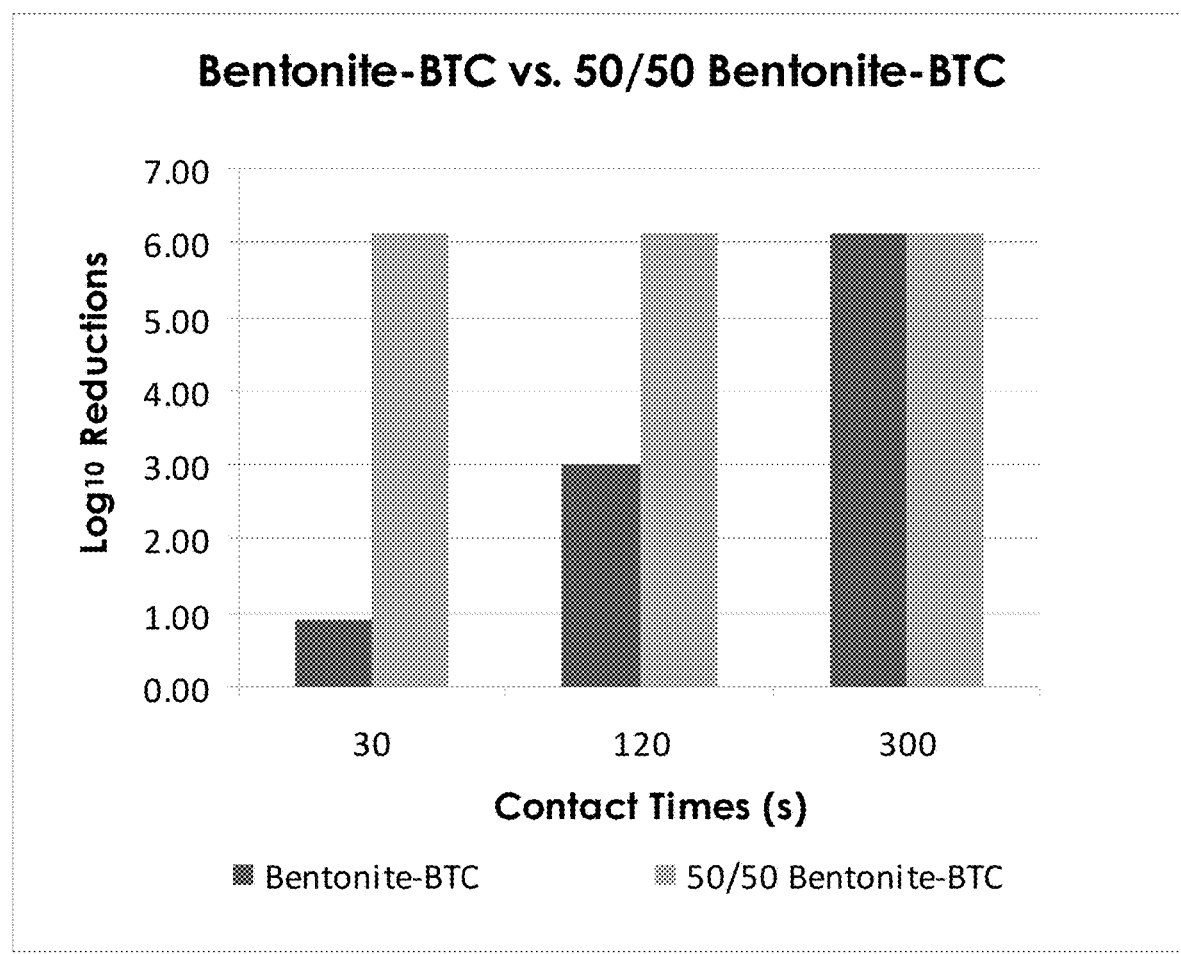
FIG. 1 is a bar graph showing that BTC (benzethonium chloride) bound to bentonite exhibits a sustained kill whereas the free BTC showed a fast kill of S. aureus.

As used herein, the term "dispersion" refers to a stable suspension. Such dispersions may be stable due to particle size and/or the presence of components having both hydrophilic and hydrophobic sites, e.g., as in a surfactant or emulsifier.

As used herein, the terms "continuous phase" and "dispersed phase" are related to a dispersion system, in which a first material is dispersed within a second material fine solid or liquid particles. In such a dispersion system, the term "continuous phase" refers to a first phase surrounding a second “dispersed phase.” The “dispersed phase” refers to the suspended particles or liquid droplets dispersed in the continuous phase.

As used herein, the term “emulsion” refers to a heterogeneous system consisting of a continuous phase and a non-continuous phase capable of forming droplets in the continuous phase.

As used herein, the term “emulsifier” refers to an agent that can reduce and/or eliminate the surface and the interfacial tension in a two-phase system. The emulsifier agent may possess both hydrophilic and lipophilic groups. The emulsifier may be considered to be either in the continuous phase, dispersed phase, or both.

As used herein, the phrase “in association with” is intended to include any or all of: chemical combination, charge attraction, entrapment, whole or partial dissolution, and suspension.

As used herein, the term “topically” refers to application of the compositions of the present invention to the surface of the skin, a wound, and/or mucosal cells or tissues (e.g., alveolar, buccal, lingual, masticatory, or nasal mucosa, etc.).

As used herein, the term "active ingredient" or "active compound" refers to an ingredient or compound having an intended biological effect. "Active ingredient" may be broadly construed to include an active compound and vice versa. Such active ingredients or active compounds are thus considered to be "biologically active".

As used herein, the term "humectant" refers to a hygroscopic compound having a plurality of hydrophilic groups (e.g., glycerin (glycerol), propylene glycol, etc.).

As used herein, the term "moisturizer" refers to a composition that, when applied to a surface (e.g. skin, mucosal tissue, wound, etc.) causes retention of water within the surface.

DETAILED DESCRIPTION OF THE INVENTION

The present invention relates to the field of carrier and delivery systems for active molecular compounds. In particular, the present invention provides aqueous dispersions for delivery of active molecular compounds.

In some embodiments, the present invention provides a dispersion comprising a dispersed phase within a continuous or aqueous phase. In some embodiments, a continuous phase comprises a liquid or gel, and may optionally comprise one or more of a humectant, emollient, detackifier, moisturizer, thickener, chelating agent, or other additive. In some embodiments, a dispersed phase comprises: a hydrophilic particle substrate having electrically charged binding sites, an intermediate component comprising a hydrophobic moiety and an ionic moiety (e.g. electrically charged moiety, hydrophilic moiety), and an active agent (e.g., biologically active agent (e.g., antimicrobial agent, etc.) comprising a hydrophobic moiety. In some embodiments, the ionic moiety of the intermediate component is attracted to the electrically charged binding sites of the hydrophilic particle substrate. In some embodiments, the hydrophobic moiety of the intermediate component is attracted to the hydrophobic moiety of the active agent. In some embodiments, attractive forces between the intermediate component and both the hydrophilic particle substrate and active agent cause the components to assemble into a complex or supermolecular particle.

In some embodiments, the present invention provides dispersions for topical administration (e.g. administration to skin, mucosal tissues, wounds, etc.). In some embodiments, when the dispersion of the invention is used topically, the dispersion includes ingredients desired or needed for the intended topical use of the composition, e.g., an alcohol such as ethanol or isopropanol, a humectant, a moisturizer, a thickening agent or mixtures thereof with each other or with other ingredients dissolved or suspended in the continuous aqueous phase. It is to be understood that such ingredients may be dissolved or suspended in the continuous aqueous phase and/or may be in association with other components suspended in the aqueous phase. Emulsifiers, e.g., chosen from cetyl alcohol and nonionic emulsifying waxes, may be considered to be in the aqueous phase or in partial solution with both the continuous aqueous phase and dispersed phase when the dispersed phase includes hydrophobic droplets. In some embodiments, humectants for use with the present invention include, but are not limited to: glycerol, propylene glycol and mixtures thereof and are usually in the continuous aqueous phase. In some embodiments, moisturizers for use with the present invention include, but are not limited to: combined gluconolactone and sodium benzoate, glycerin, and olive oil where hydrophobic moisturizers are suspended in the aqueous phase either alone or in association with suspended particles. In some embodiments, a thickener is a gelling agent (e.g., gelatin or collagen).

Dispersions

In some embodiments, compositions (e.g. dispersions) have viscosities of at least 100 centipoise (e.g., >100 centipoise, 100-150 centipoise, 150-200 centipoise, >200 centipoise, 200-300 centipoise, >300 centipoise, >500 centipoise). In some embodiments, compositions have viscosities of 150-200 centipoise. In some embodiments, compositions have viscosities of greater than about 1000 centipoise (e.g., 1000 centipoise . . . 2000 centipoise . . . 5000 centipoise . . . 10,000 centipoise . . . 20,000 centipoise . . . 50,000 centipoise . . . 100,000 centipoise . . . 200,000 centipoise, etc.). In some embodiments, compositions are gels. In some embodiments, desired viscosities are obtained by inclusion of gelling agents, high viscosity additives, and increase concentration of solids (e.g., >10%, >15%, >20%, >25%, >30%, >40%, >50%, etc.).

In some embodiments, a dispersion has a continuous aqueous phase containing particulate material held in suspension by small particle size, e.g., sub-micron, or by an emulsifier. In some embodiments, a dispersion has a suspended phase including suspended microparticles or smaller and may include hydrophobic droplets. The droplets and sometimes solid particles, may be held in suspension with the assistance of an emulsifier. In some embodiments, "continuous aqueous phase" or "aqueous phase" refers to the continuous phase surrounding solid particle and/or hydrophobic droplets. The aqueous phase thus contains suspended or dissolved components, e.g., thickeners, gelling agents, humectants, moisturizers, emulsifiers, chelating agents, stabilizers, adherents, emollients, dyes and fragrances. Emollients and emulsifiers may be considered as being in an intermediate phases between aqueous (polar) and non-polar (oil) phases. The particles and hydrophobic droplets may be considered to be the suspended phase. The water used to form the aqueous phase is deionized water obtained by any known means, e.g., ion exchange resins or distillation in an inert system, e.g., in non-reactive glass, or reverse osmosis.

In some embodiments, the compounds used for the intermediate components comprise ligands, i.e., bound to the central particle and arranged to accept additional components at exposed portions. In some embodiments, compound for use in an intermediate layer is a quaternary ammonium compound having a hydrophobic tail; although, any other compound having an ionic structure may be used and attracted as above described.

Ligands having antimicrobial properties include compounds having reactive inorganic cations, particularly those which have one or more electrons available for chemical reactions (e.g., transition metals) and compounds containing organic cations known to have bactericidal activity. For example, the antimicrobial effects of quaternary ammonium compounds, iodophor compounds, phenolics, alcohol, chlorine, peroxides, aldehydes and metals have been well documented. For further detail, see U.S. Pat. No. 6,288,076, which is hereby incorporated by reference in its entirety. Ligands having antimicrobial properties which are particularly desirable for use as ligands in the present invention include quaternary ammonium compounds, transition metals, organo metallic compounds, perchlorates, charged halogen-containing compounds, charged organic peroxides, ionic polymers, ionic surfactants, and mixtures thereof.

Especially desirable quaternary ammonium compounds include hexadecyltrimethyl ammonium bromide, trimethylphenyl ammonium chloride, and mixtures thereof. Especially desirable transition metals include copper, iron, manganese, zinc, silver, mercury, and mixtures thereof. The antimicrobial agent of the present invention includes ligands attached to the colloidal particles in excess of and up to 200% of the C.E.C. of the colloid particles, resulting in greater efficacy of the antimicrobial agent.

A preferred quaternary compound having cationic activity is benzethonium chloride. Benzethonium chloride, having an ionic hydrophilic site and a hydrophobic tail and being an antimicrobial and thus active may be used in both the secondary and tertiary layers. The benzethonium chloride may be present in an amount of 0.5% by weight of solids.

Quaternary ammonium compound may be used as a secondary layer and/or an antimicrobial tertiary layer, e.g., in an amount of 0.50% by weight of solids.

When compounds have such properties they may be directly and indirectly loaded onto the particle substrate in two layers. Complete loading on a single layer may be considered as a 100% loading and when complete loading occurs on both the intermediate secondary and tertiary layers, loading may be considered to be 200%. The present invention may permit loading as high as 200% or even higher due to additional complex interactions.

In some embodiments, the present invention provides particle substrates. In some embodiments, particle substrates comprise hydrophilic particle substrates. In some embodiments, particle substrates comprise hydrophilic submicron particle substrates. In some embodiments, particle substrates comprise electrically charged binding sites. In some embodiments, particle substrates comprise hydrophilic sites (e.g., hydrophilic binding sites). In some embodiments, hydrophilic sites are due to ionic moieties, e.g., a quaternary, carboxy, sulfo, phosphor, or a polar component such as may be found in a chemically bound oxygen, nitrogen, sulfur or phosphorous atom having an exposed electron pair. Such components may be compounds or aggregations. Particular examples are anionic, cationic and non-ionic groups as may be found in surfactants. In some embodiments, particle substrates have submicron diameters (e.g., <1 µm, <0.5 µm, <0.2 µm, <0.1 µm, <0.05 µm, <0.02 µm, <0.01 µm, etc.). In some embodiments, submicron size provides stability. In some embodiments, submicron particles are nanoparticles that require no stabilization.

As used here, the term "particle substrate" means a particle that acts as a substrate for an interaction with an agent, compound, ligand, reactive group, functional group, etc. An example of particle substrates that find use in the present invention is a hydrophilic hydrated clay. Such clays are primarily aluminosilicates in which some of the aluminium and silicon ions have been replaced by elements with different valence, or charge. For example, aluminium ($Al^{3+}$) may be replaced by iron ($Fe^{2+}$) or magnesium ($Mg^{2+}$), leading to a net negative charge. This charge attracts positive cations which in turn may attract a corresponding anion.

The particles may be organic and inorganic particles, including nano-particles. Preferred inorganic materials have surface areas ranging from 50-1000 $m^2$/gm, with surface areas of 500-800 $m^2$/gm being especially desirable. Useful synthetic types of clay-type minerals include a synthetic hectorite, which is a layered hydrous magnesium silicate, such as LAPONITE (Southern Clay Products, Gonzales, Tex.), a synthetic mica-montmorillonite, such as BARA-SYM, (Baroid Division, NL Industries, Houston, Tex.) and mixtures thereof. Useful naturally occurring clay minerals include swelling clays such as aliettite, beidellite, bentonite, nontronite, saponite, sauconite, stevensite, swinefordite, volkonskoite, yakhontovite, hectorite, montmorillonite (such as BP colloid), and mixtures thereof. Other useful materials (both synthetic and naturally occurring) include, but are not limited to polymers, zeolites, layered double hydroxides, illite, chlorite, kaolinite, hydrotalcite, talc, halloysite, sepiolite, and palygorskite, as well as other minerals such as oxides, hydroxides, and silicates, to name just a few. Typically, the colloid particles of the present invention have a mean diameter of 1 nm to 100 microns, having mean diameters of less than 2 microns with diameters of less than one micron being preferred.

Preferred clays are hydrophilic smectite, laponite and bentonite clays having high cationic exchange properties. Other suitable particles are ion exchange resin particles, and organic plastic particles having charged sites.

In some embodiments, particles are characterized by both large surface areas and substantial ion exchange capacities. Such ion exchange capacities are usually, but not always cation exchange capacities (CEC). It is to be understood that anion exchange resins may also be used, e.g., polyfunctional resins containing quaternary amine groups. In general where "CEC" is used herein, it should be understood that anion exchange resins may also be used in the appropriate context. The number of binding sites on a particle may be determined by binding sites per mole when the structural formula of the resin is known as modified by surface characteristics, e.g., surface area due to particle sizes effects. A number of CEC's are known for particular materials, e.g., for laponites used in examples herein are known to have a CEC of about 55.0 meq/100 grams. Compositions provided herein are unique in that loadings well in excess of the CEC may be obtained, e.g., over 125% up to as much as 250% or more. Loadings in excess of 150% are readily obtained.

Bioactive compositions, e.g., antimicrobial compositions, made according to the methods of the present invention use a variety of substrates, examples of which are given below, in addition to a variety of bioactive compounds that are attached to the substrate. By varying the organics that are used for ion exchange to prepare the organo-substrate, the organo-substrate can be tailored to have either hydrophilic or hydrophobic surface tension properties. Furthermore, by choosing the appropriate carrier substrate, e.g., clay, that is used for additional attachment of organic onto the organo-substrate, the antimicrobials produced can exhibit either hydrophilic or hydrophobic properties. This allows the antimicrobials to be used in either aqueous or non-aqueous formulations.

In certain embodiments, active agents comprise a tertiary layer of particulates of the present invention. In some embodiments, active agents (e.g., molecules for forming the tertiary layer) have a hydrophobic moiety (e.g., hydrophobic tail). In other embodiments, active agents (e.g., molecules for forming the tertiary layer) have a biologically active moiety. In particular embodiments, active agents are quaternary compounds. In some embodiments, active agents are antimicrobials, humectants, moisturizers, anti-inflammatory, and nutrients.

In some embodiments, a quaternary compound comprises one or more antimicrobial agents, including, but not limited to: lauryl dimethyl benzylammonium chloride, benzalkonium chloride, alkyltrimethyl ammonium chloride, dialkyldimethylammonium chloride, alkyldimethylbenzylammonium chloride, alkyldimethyl(ethylbenzyl)ammonium chloride, combinations thereof, etc. In other embodiments, a quaternary compound comprises one or more non-antimicrobial conditioning agents, including, but not limited to: cetrimide, cetrimonium bromide, cetylamidopropyldimethyl ammonium chloride, stearyl trimethyl ammonium chloride, stearalkonium chloride, dihydrogenated tallow dimethyl ammonium chloride, combinations thereof, etc.

In various embodiments, a dispersion comprises one or more sunscreens and/or UV-blocking agents, including, but not limited to: octyl methoxycinnamate, octyl salicylate, titanium dioxide, avobenzone, benzophenone 4, combinations thereof, etc.

Specific, non-limiting examples of suitable hydrophobic active ingredients are: acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. In addition, salts, isomers and derivatives of the above-listed hydrophobic active ingredients may also be used, as well as mixtures.

Dispersions may comprise additional compounds including, but not limited to, emulsifiers, chelating agents, gelling agents, stabilizers, adherents, emollients, dyes, detackifiers, thickeners, nonaqueous moisturizers, anti-inflammatory agents, skin adherents, and fragrances.

Dispersions may also comprise a detackifier such as phenyl substituted silicone fluid, e.g., phenyl trimethicone. In some embodiments, a detackifier also acts as a humectant. In some embodiments, dispersions comprise an emollient, e.g., pentaerythrityl tetracaprylate.

In certain embodiments, a dispersion comprises one or more dyes and/or pigments, including, but not limited to: titanium dioxide, natural minded and synthetic iron oxides, blends of inorganic oxides and fillers (kaolin, talc, silica, mica), D&C colors, FD&C colors, combinations thereof, etc. In some embodiments, a dispersion comprises one or more dyes, including, but not limited to: Disperse Red 13, Disperse Green 9, Solvent Black 3, Disperse Blue 148, Disperse Violet 63, Disperse Blue, Disperse Blue 14, Solvent Orange 15, Solvent Orange 7, Solvent Blue 14, Disperse Yellow 82, 9-diethylamino-5H-benzo[alpha]phenoxazine-5-one, 1-dimethylamino-5-sulfamoylnaphthalene, pyrene, 1-pyrenecarbaldehyde, Reichardt's dye, 4-aminophthalimide, 4-(N,N-dimethylamino)phthalimide, bromonapthalene, 2-(dimethylamino)naphthalene, solvatochromatic dye, combinations thereof, etc.

In particular embodiments, a dispersion comprises one or more fragrances, including, but not limited to: tea tree oil, citrus oils (e.g., lemon oil, orange oil, etc.), oils from herbs (e.g., rosemary, oil, thyme oil, oregano oil, etc.), oils from woods (e.g., rosewood oil, cedarwood oil), cinnamaldehydes or cinnamon bark oil, eugenol or clove flower oil, cineol or eucalyptus oil, camphor or camphor tree oil, geraniol or palmarosa oil, citronella oil, geranium oil, cedrol, etc. In some embodiments, the present invention provides any suitable essential oil. In some embodiments, fragrances further provide antimicrobial, fungicidal, and/or insect-repelling functionality.

In some embodiments, a dispersion comprises one or more emulsifiers, including, but not limited to: PEG-dimethicones, polyglycerol dimethicones, Sorbian oleate, glyceryl esters, C12-15 alkyl benzoate, castor oil, cetearyl alcohol, cetyl alcohol, cetyl esters, cetyl palmitate, diisopropyl adipate, emu oil, isopropyl myristate, isopropyl palmitate, lanolin, *Mangifera indica* seed butter, mineral oil, myristyl myristate, sorbitan oleate, safflower oil, shea butter, stearic acid, stearyl alcohol, calcium stearoyl lactylate, ceteareth-20, cocamide MEA, glyceryl laurate, glyceryl stearate, glyceryl stearate and PEG-100 stearate, glyceryl stearate SE, glycol distearate, glycol stearate, isoceteth-20, isosteareth-20, lauramide DEA, laureth-23, laureth-4, linoleamide DEA, methyl glucose sesquistearate, oleth-10, oleth-10/polyoxyl 10 oleyl ether NF, Oleth-2, Oleth-20, PEG-100 Stearate, PEG-20 Almond Glycerides, PEG-20 Methyl Glucose Sesquistearate, PEG-25 Hydrogenated castor oil, PEG-30 dipolyhydroxystearate, PEG-4 dilaurate, PEG-40 sorbitan peroleate, PEG-60 almond glycerides, PEG-laurate, PEG-80 sorbitan laurate, polysorbate 20, polysorbate 60, polysorbate 80, polysorbate 85, sodium stearoyl lactylate, sorbitan isostearate, sorbitan laurate, sorbitan sesquioleate, sorbitan stearate, sorbitan stearate and sucrose cocoate, sorbitan trioleate, stearamide MEA, steareth-2, steareth-21, combinations thereof, etc.

Dispersion may comprise one or more humectants, including, but not limited to: polyglycerol dimethicones, gelatin, glycerin, honey, hyaluronic acid, panthenol, propylene glycol, sodium ammonium lactate, sodium pyrrolidine carboxylic acid, sorbitol, urea, 1,2,6 hexanetriol, Hexylene and Butylene Glycol, Dipropylene glycol, Hexylene Glycol, Panthenol, Phytantriol, Sodium PCA, Triethylene glycol, olyglyceryl sorbitol, Glucose, Fructose, Polydextrose, Potassium PCA, Hydrogenated Honey, Inositol, Hexanediol beeswax, Hexanetriol Beeswax, Hydrolyzed Elastin, Hydrolyzed Collagen, Hydrolyzed Silk, Hydrolyzed Keratin, Erythritol, Capryl glycol, Isoceteth-(3-10, 20, 30), Isolaureth-(3-10, 20, 30), Laneth-(5-50), Laureth-(1-30), Steareth- (4-20), Trideceth-(5-50), sucrose, glucose, aloe, alpha-hydroxy acids (AHA's), combinations thereof, etc.

In some embodiments, a dispersion comprises one or more thickeners and/or stabilizers, including, but not limited to: dimethicone gums, dimethicone cross-polymers, stearic acid, stearic acid with cetyl alcohol, cellulose, carbopol, polyacrylic acid, clays, carrageenan, pectin, and locust bean gum, xanthum gum, carbomer (a homopolymer of acrylic acid with a high molecular weight, which is cross-linked with any of several polyalcohol allyl ethers), combinations thereof, etc.

In certain embodiments, a dispersion comprises one or more detackifiers and/or emollients, including, but not limited to: dimethicone cross-polymers, cyclomethicone, plant oils, polyisobutene, squaline, ceramides like lacto-ceramide, essential fatty acids (linoleic acid), fatty acids and esters of fatty alcohols and fatty acids, lanolin, lauric acids, stearic and palmitic acids with carbon chains lengths of 16 and 18 (coconut oil, grapeseed oil, and palm kernel oil), ceramides, combinations thereof, etc. In some embodiments proteins are providedthat, like emoillents, shrink on the skin (or a wound) leaving a film that smoothes the skin, thereby avoiding water loss (e.g., collagen, keratin, elastin, protein mixtures like wheat protein).

In various embodiments, a dispersion comprises one or more alcohols, including, but not limited to: acyclic alcohols (e.g., ethanol), isopropyl alcohol, etc.

In other embodiments, a dispersion comprises one or more adherents and/or film formers, including, but not limited to: trimethylsiloxysilicates, acrylates/dimethicones, etc.

In some embodiments, a dispersion comprises one or more conditioners, including, but not limited to: dimethicone gums, amine modified silicones, cetrimide, cetrimonium bromide, cetylamidopropyldimethyl ammonium chloride, combinations thereof, etc.

In particulat embodiments, a dispersion comprises one or more preservatives, including, but not limited to: Phenonip, Parabens and esterof parabenzoic acids (phenoxyethanol), antioxidants (tocopherol, BHT, combinations thereof, etc.

In various embodiments, a dispersion comprises one or more oils and/or waxes, including, but not limited to: aleurites moluccana seed oil, almond oil NF, anhydrous lanolin USP, apricot kernel oil, avocado oil, babassu oil, beeswax, borage seed oil, brazil nut oil, *Cannabis sativa* seed oil, canola oil, caprylic/capric triglyceride, carrot seed oil, ceresin, coconut oil, *Daucus carota sativa* root extract, dimethicone, dog rose hips oil, evening primrose oil, grape seed oil, hybrid safflower oil, jojoba oil, macadamia nut oil, *Mangifera indica* seed butter, olive oil, *Oryza sativa* oil, peanut oil NF, petrolatum, PPG-15 steryl ether, retinyl palmitate, sesame oil, soybean oil, sunflower oil, sweet almond oil, *Theobroma cacao* seed butter, tocopherol, combinations thereof, etc.

In some embodiments, the compositions may also contain a moisturizing agent (moisturizer). Moisturizers prevent and treat dry skin, protect sensitive skin, improve skin tone and texture, and mask imperfections. Moisturizers are often complex mixtures of chemical agents specially designed to make the external layers of the skin (epidermis) softer and more pliable, by increasing its water content by reducing evaporation. Naturally occurring skin lipids and sterols, as well as artificial or natural oils, humectants, emollients, and lubricants, for example may be part of the moisturizer composition. One example of a moisturizing substance that is used in the present invention is glycerin. Other skin moisturizers that are considered for use in the present invention include, but are not limited to: urea, ammonium lactate, NaPCA, saccharides, simple sugars, hydroscopic salts and glycerin, often found in combination with an emollient such as *Butyrospernum Parkii* (Shea butter) fruit, *Glycine soja* (soybean) sterol and *Helianthus Annuus* (hybrid sunflower) oil and olive oil. As previously mentioned, another suitable moisturizer is gluconolactone combined with sodium benzoate.

Chelating agents, e.g., a gluconate, may be used to chelate substances that may interfere with desired reactions and combinations, e.g., The chelating agent may be present to attract compounds that may interfere with the binding of the quaternary compound with the colloidal substrate Chelating agents are not usually required. A chelating agent, e.g., 20% of a 60% solution of gluconic acid and sodium gluconate as determined after neutralization, may be present.

Some embodiments provide dispersions in the form of a topical antimicrobial carrier system wherein the particulate material includes a hydrophilic clay, the secondary layer comprises a quaternary ammonium compound and the tertiary layer comprises an antimicrobial compound. In some embodiments, dispersions comprise a quaternary compound such as benzethonium chloride. In some embodiments, dispersions are in the form of a topical anti-inflammatory composition, e.g., where the tertiary layer contains an anti-inflammatory compound such as an omega 3 fatty acid. In some embodiments, dispersions are in the form of a topical analgesic, e.g., where the tertiary layer contains capsaicin or lidocaine.

In some embodiments, the present invention provides an antimicrobial system dispersion including an aqueous continuous phase containing at least one of an alcohol, a humectant, a moisturizer, and a thickening agent; a hydrated particulate hydrophilic clay as the submicron particulate substrate; a quaternary compound having a quaternary group providing cationic activity attached to a hydrophobic tail for providing molecules in the secondary layer for acceptance of molecules for forming the tertiary layer. The invention may further include the dispersion including the tertiary layer.

In certain embodiments, a carrier system of the present invention is an antimicrobial carrier system including, but not limited to: a hydrophilic clay, a quaternary compound having cationic activity, a moisturizer and an emulsifier. In some embodiments, the hydrophilic clay is selected from the group consisting of a hectorite, laponite, bentonite and mixtures thereof. In some embodiments, the quaternary compound is benzethonium chloride. In some embodiments, the moisturizer is olive oil. In some embodiments, the emulsifier is a nonionic emulsifying wax.

Dispersions of the present invention provide significant advantages over administration of active agents via other carriers and/or systems, including, but not limited to: reduction of toxicity of active ingredients, extended time of activity for active ingredients, time release characteristics, controlled release of active ingredients, ease of use, increased active ingredient loads of up to 200% of ion exchange capacity or greater, reduced irritation and enhanced effectiveness.

The method of the present invention may include the steps of combining a hydrophilic clay in the form of particles having charged sites, with a compound having an ionic moiety and a hydrophobic tail to form a pre-combination and introducing the pre-combination into an aqueous phase to obtain an intermediate dispersion and combining a hydrophobic active compound with the intermediate dispersion to obtain further dispersion of particles having a substrate particle combined with an intermediate secondary layer having a hydrophobic tail and a tertiary layer including the active compound.

Further examples of detailed methods of making and using a dispersion of the invention include, but are not limited to the following. In certain embodiments the present invention provides methods of making an antimicrobial carrier system including one or more of the steps of: adding a humectant to deionized water to form an aqueous suspension; uniformly mixing a hydrophilic clay and a quaternary compound; adding water to the resulting clay and quaternary compound mixture to form a hydrophilic clay-quaternary ammonium compound combination; combining the aqueous suspension and the hydrophilic clay-quaternary ammonium compound combination to obtain a suspension; heating the suspension to between 70 and 90° C.; dispersing together at least one of a gelling agent, a skin adherent, a humectant, a detackifier, a nonaqueous moisturizer, an anti-inflammatory, an emollient, and an emulsifier to obtain a dispersion; heating the dispersion to between 70 and 90° C.; mixing the dispersion with the suspension; drawing a vacuum; and homogenizing the resulting composition. In some embodiments the present invention provides methods of making a carrier system for a biologically active compound having a cationic moiety and a hydrophobic moiety including one or more of the steps of: mixing the biologically active compound and a hydrophilic clay to form an active compound-hydrophilic clay mixture; suspending the active compound-hydrophilic clay mixture in an aqueous liquid to form a suspension; and incorporating the suspension into a carrier including at least one of a gelling agent, a skin adherent, a humectant, a detackifier, a moisturizer, an anti-inflammatory, an emollient, and an emulsifier. Any of the above or following methods may include adjusting pH if necessary, e.g., by adding KOH to mixed contents to adjust the pH to from about 5.2 to 6.2.

The invention also includes a method for topically disinfecting an epidermal surface including the step of contacting the epidermal surface with a composition of the invention where a tertiary layer contains an antimicrobial compound.

In a further embodiment, the invention includes a method of topically applying a medicament to an epidermal surface comprising applying a composition of the invention wherein a tertiary layer contains the medicament.

The present invention finds use in a variety of applications and compositions. Exemplary applications and compositions are provided below. These should not be viewed as limiting; rather, the alterations and combinations of these embodiments are within the scope of the invention.

Embodiments of the present invention provide antimicrobial creams, lotions, gels, ointments, and or liquids for application to the skin of a subject (e.g., antimicrobial hand cream). Such an embodiment, as well as others provided herein, finds use with subjects, including, but not limited to: healthcare workers, nurses, doctors, surgeons, patients, pre- and post-operative patients, schools, teachers, students, travelers, flight attendants, sanitation workers etc. Antimicrobial compositions (e.g. hand creams or gels) may find use in protecting against the spread of and/or killing a wide variety of pathogens including, but not limited to: gram positive bacteria (e.g., *Staphylococcus aureus*, Methicillin-resistant *Staphylococcus aureus, Staphylococcus epidermidis, Streptococcus faecalis, Clostridium* spp., *Listeria* spp., *Bacillus* spp., etc.), gram negative bacteria (e.g., *E. coli, Serratia marcescens, Pseudomonas aeruginosa, Salmonella* spp., *Helicobacter, Acinetobacter Baumanii*, etc.), yeast (e.g., *Candida albicans, Cryptococcus Neoformans, Candida glabrata*, etc.), mold (e.g., *Aspergillus niger, Cladosporium, Acremonium*, etc.), viruses (e.g., Adenovirus, Influenza virus, Rotavirus, Rhinovirus, etc.), etc. In some preferred embodiments, the active agent in antimicrobial compositions (e.g., antimicrobial hand cream) is benzethonium chloride. In other embodiments, co-active agents in antimicrobial compositions (e.g., antimicrobial hand cream) are conditioners (e.g., stearalkonium chloride, Masurf FQ20, etc.), moisturizers (e.g., ceramide, borage oil, tocopherol, tocopherol linoleate, etc.), anit-fungal agents (e.g., miconazole nitrate, metronidazole, eonazole nitrate, clotrimazole, etc.), antimicrobial agents (e.g., essential oils, quaternary ammonium compounds (e.g., benzalkonium chloride, benzoyl alcohol, chlorohexidine, Masurf FQ20, etc.)).

In further embodiments, the present invention provides wound care ointments, creams, lotions, gels, and or liquids for application to wounds of a subject (e.g., human subject, non-human animal subject). Such an embodiment, as well as others provided herein, finds use with subjects, including, but not limited to: burn patients, wounded patients/soldiers (including MRSA/VRSA patients), etc. Wound care compositions (e.g., ointments) find use in protecting against the spread of and/or killing a wide variety of pathogens including, but not limited to: *Staphylococcus aureus, Pseudomonas aeruginosa, Streptococcus pyogenes, Candida albicans*, and *Aspergillus* fumigates in burn patients; and *Staphylococcus aureus*, Coagulase-negative staphylococci, Enterococci, *Escherichia coli, Pseudomonas aeruginosa, Enterobacter species, Proteus mirabilis* and *Proteus* ssp., *Klebsiella pneumonia* and *Klebsiella* ssp., Other streptococci, *Candida albicans*, Group D streptococci, Other gram-positive aerobes, *Bacteroides fragilis, Streptococcus pyogene, Enterococcus faecalis, Clostridium*, and Bacteroids in patients with open wounds. In some embodiments, the active agents in wound care compositions include, but are not limited to: benzalkonium chloride, benzethonium chloride, benzocaine, hydrophobically modified benzocaine/lidocaine, ionic silver, activated charcoal, molecular iodine, polyhexamethyl biguanide, bacitracin, lidocaine, asiatic acid, asiaticoside, madecassic acid, *Allium cepa*, allantoin, etc.

Embodiments of the present invention provide ointments, creams, lotions, gels, and or liquids for the topical treatment of acne in a subject. Such compositions find use in treatment of acne in infants, children, adolescents, teenagers, and/or adults would suffer from various forms of acne. In some embodiments, acne-treatment compositions find use in treating and/or killing *Propionibacterium acnes, Staphylococcus aureus*, etc. In some embodiments, the active agent in acne treatment compositions include, but are not limited to: benzethonium chloride, hydrophobically modified salicylate, salicylic acid, benzoyl peroxide, acetone, tea tree oil, isotretinoin (for rosasea, cystic acne), allantoin.

Also provided herein are ointments, creams, lotions, gels, and or liquids for the topical anti-aging treatment. The active agent in anti-aging treatment compositions include, but are not limited to: retinol, palmitic acid, stearic acid allantoin, tartaric acid, lactic acid, malic acid, citric acid, glycolic acid, 3-hydroxypropanoic aid, tea extracts, copper peptides, coenzyme q10, kinetin, antioxidants, arbutin, astaxanthin, etc.

Ointments, creams, lotions, gels, and or liquids are also provided for oral hygiene. Oral hygiene compositions find use in treating and/or killing, for example: *Streptococcus mutans, Porphyromonas gingivalis, Staphylococcus epidermidis, Streptococcus salivarius, Lactobacillus* sp., *Streptococcus sanguis, Treponema denticola*, Fusospirochetes, *Veillonella*, Aggregatibacter *actinomycetemcomitans* etc. Active agent in oral hygene compositions include, but are not limited to: thymol, eucalyptol, hexetidine, methyl salicylate, menthol, chlorhexidine gluconate, benzalkonium chloride, cetylpyridinium chloride, benzethonium chloride, methylparaben, hydrogen peroxide, domiphen bromide, fluoride, enzymes, calcium, xylitol, etc.

Other embodiments provide ointments, creams, lotions, gels, and or liquids for the topical anti-itch treatment. Active agents in anti-itch treatment compositions include, but are not limited to: benzethonium chloride, isotretinoin (for rosasea, cystic acne), clotrimazole, steroids (corticosteroid), hydrocortisone, allantoin, econasole nitrate, etc.

In some embodiments, the present invention provides ointments, creams, lotions, gels, and or liquids for analgesic treatment. Active agents in analgesic compositions include, but are not limited to: benzethonium chloride, lidocaine, benzocaine, hydrophobically modified benzocaine/lidocaine, aspirin, benzoyl alcohol, camphorated metacresol, chlorobutanol, etc.

In certain embodiments, the present invention provides ointments, creams, lotions, gels, and or liquids for antiperspirant/deodorant applications. Active agents in antiperspirant/deodorant compositions include, but are not limited to: aluminum salts, titanium salts, chloroacetic acid, sodium bicarbonate, zinc bicarbonate, ethyl citrate, chlorohexidine gluconate, glycerol ether, propyl p-hydroxybenzoate, etc.

In other embodiments, the present invention provides ointments, creams, lotions, gels, and or liquids for insect repellants to be applied to the skin of a subject. Active agents in insect repellants compositions include, but are not limited to: N,N-Diethyl-meta-toluamide, other pesticides <carbaryl, permethrin>, essential oils (e.g., oil of citronella, etc.), etc. In some embodiments, the co-active agents in insect repellants compositions include, but are not limited to: p-aminobenzoic acid, padimete O, phenylbenzimidazole sulfonic acid, cinoxate, Titanium dioxide, dioxylbenzone, oxybenzone, homosalate, menthyl anthranilate, octocrylene, octyl methoxycinnamate, octyl salicylate, sulisobenzone, trolamine salicylate, avobenzone, ecamsule, zinc oxide, tinosorb M, tinosorb S, mexoryl XL, benzophenone-9

In other embodiments, the present invention finds use as a carrier for agents for specific applications, including treatment and/or prevention of specific pathogens, conditions, or diseases including, but not limited to: delivery of acyclovir for treatment of herpes, delivery of docosan-1-ol for treatment of cold sores, delivery of minoxidil to slow/stop hair loss, or delivery of cinnamon leaf essential oil, dipalmitoyl hydroxyproline, palmitoyl oligopeptide, etc.

It should be noted that the disclosed invention is disposed to embodiments in various formulations, such as liquids, creams, lotions, and sprays. Therefore, the embodiments described herein are provided with the understanding that the present disclosure is intended as illustrative and is not intended to limit the invention to the embodiments described.

It is to be understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims. Although any methods, devices or materials similar or equivalent to those described herein can be used in the practice or testing of the invention, they should not be viewed as limiting.

EXPERIMENTAL

Example I

In experiments conducted during development of embodiments of the present invention, in vivo tests using human hands showed that alcohol sanitized hands can become re-contaminated even without coming in contact with a contaminated surface. Microorganisms were identified on alcohol sanitized hands as early as 30 and 60 seconds after application of an alcohol based sanitizer and without the hands having touched a contaminated surface. The test protocol for all the Examples discussed here and below was as follows. Prior to sanitization, each subject's palms and 3 finger tips were placed on an agar slide to demonstrate pre sanitization microbial contamination. Tryptic soy agar with appropriate neutralizers was used as the growth medium. Then each subject applied alcohol based hand sanitizer, rubbed it in thoroughly and allowed it to dry. After 30 seconds and not touching anything, each subject's sanitized palms and 3 finger tips were again placed on an agar slide. After an additional 30 seconds, that is a full minute from application, the subjects' palms and 3 finger tips again were again placed on agar slides. The slides were incubated at 37° C.±1° C. for 18 to 24 hours. The results show that recontamination can occur in as little as 60 seconds even without surface contact.

There appears to be a 2.0 log reduction (85.53%) 30 seconds after treatment with the alcohol based sanitizer followed by a 1.9 log reduction (79.90%) after 60 seconds indicating the effectiveness of the sanitizer was decreased only 60 seconds after application to the finger tips and palms of the subjects.

Example II

Experiments were conducted during development of embodiments of the present invention to determine the difference in microbial reduction between an active ingredient bound to clay and a mixture of bound and free actives. A bentonite clay-benzethonium chloride (BTC) slurry was mixed by hydrating the clay in water, adding BTC solubilized in water, centrifuging and decanting the supernatant. Table 1 shows the quantities used:

TABLE 1

|  | Bentonite-BTC Slurry g (w/w) |
|---|---|
| DI | 1973.98 |
| Bentonite | 53.76 |
| BTC | 16.56 |

Both were added to an oil phase having the following components:

| OIL PHASE | % |
|---|---|
| 200 Fluid 500 CST (Corning) polydimethylsiloxane | 2.50 |
| SF1550 (GE/Bayer) phenyltrimethicone | 2.50 |
| Mineral Oil | 3.00 |

-continued

| OIL PHASE | % |
|---|---|
| COSMOWAX J (Croda) cetearyl alcohol | 6.00 |
| Cetyl Alcohol | 7.00 |

Table 2 shows the proportions of the BTC slurry in the bound and free/bound mixtures:

TABLE 2

| | Bentonite-BTC % (w/w) | 50/50 Bentonite-BTC % (w/w) |
|---|---|---|
| WATER PHASE 1 | 33.55 | 53.28** |
| WATER PHASE 2 | 39.95 | 19.975 |
| Bentonite-BTC Slurry* | | |
| Free BTC | 0 | 0.25 |
| OIL PHASE | 26.5 | 26.5 |

The Time Kill results are seen in Table 3:

TABLE 3

| | Bentonite-BTC | | 50/50 Bentonite - BTC | |
|---|---|---|---|---|
| contact time (s) | S. aureus 6538(CFU/mL) | $Log_{10}$ Reductions | S. aureus 6538(CFU/mL) | $Log_{10}$ Reductions |
| 0 | 1.2E+06 | | 1.2E+06 | |
| 30 | 2.0E+05 | 0.92 | 0.0E+00 | 6.12 |
| 120 | 1.0E+03 | 3.02 | 0.0E+00 | 6.12 |
| 300 | 0.0E+00 | 6.12 | 0.0E+00 | 6.12 |

As seen in FIG. 1, the fully bound BTC exhibits a sustained kill whereas the free BTC showed a fast kill.

A similar test was conducted using a second synthetic clay, laponite, to form mixtures of bound BTC and a combination of free and bound BTC. The laponite mixtures were formed similarly to the bentonite described above. The Time Kill results are seen in Table 4:

TABLE 4

| | Laponite-BTC | | 50/50 Laponite - BTC | |
|---|---|---|---|---|
| contact time (s) | S. aureus 6538(CFU/mL) | $Log_{10}$ Reductions | S. aureus 6538(CFU/mL) | $Log_{10}$ Reductions |
| 0 | 1.2E+07 | | 1.2E+07 | |
| 30 | 2.3E+06 | 0.89 | 1.7E+06 | 0.95 |
| 120 | 1.1E+06 | 1.00 | 1.7E+05 | 1.95 |
| 300 | 4.8E+05 | 1.64 | 2.2E+04 | 2.90 |

Figure 2:
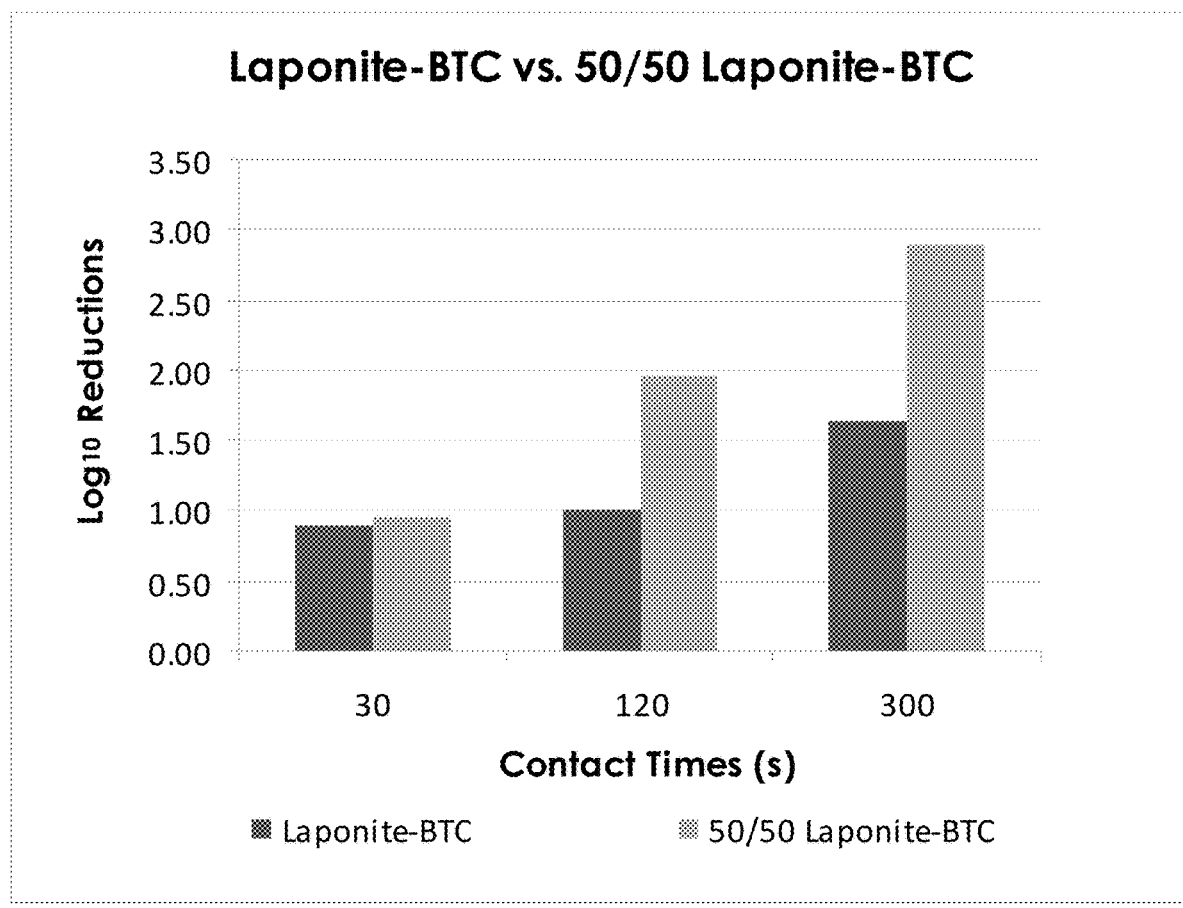
FIG. 2 is a bar graph showing that BTC bound to LAPONITE clay exhibits a sustained kill whereas the free BTC showed a fast kill of S. aureus.

The graph shown in FIG. 2 compares the bound and free (50/50) results:

Example III

A commercially available hydrophobically modified polymer, Polymer SK-M from Dow (polyquaternium 67, quaternized hydroxyl ethyl cellulose modified with dimethyl-dodecyl hydrophobic functionality to prevent solution but retaining significant hydrophilic function), was used to replace the natural clays used in the examples discussed above. An SK-M-BTC slurry was formed by dry mixing BTC and SK-M then hydrating overnight in water. In an alternate mixing method, SK-M was expanded in hot water and cooled after adding the remaining water. BTC was then added and allowed to sit overnight. A mixture was formed adding the slurry to a water-GEOGUARD ULTRA-gluconate mixture to complete the water phase. GEOGUARD ULTRA (Lonza) is a preservative containing glucolactone and sodium benzoate. The completed water phase was then added to the oil phase. The complete mixture ingredients were:

TABLE 5

| | % |
|---|---|
| Polymer SK-M, BTC SLURRY | |
| DI (QS) | 93.00 |
| BTC USP | 5 |
| Polymer SK-M | 2.00 |
| total | 7.00 |
| WATER PHASE | |
| DI (QS) | 60.80 |
| GEOGARD ULTRA | 2.00 |
| Gluconate | 0.20 |
| WATER PHASE 2 | |
| Polymer SK-M, BTC slurry | 10.00 |
| OIL PHASE | |
| Olive oil | 13.50 |
| COSMOWAX J | 13.50 |
| ADJUSTMENTS | |
| KOH | q.s. |

The Time Kill results are shown in Table 6:

TABLE 6

| | POL101 | |
|---|---|---|
| contact time (s) | S. aureus 6538 (CFU/mL) | $Log_{10}$ Reductions |
| 0 | 4.5E+09 | |
| 30 | 8.5E+05 | 3.60 |
| 60 | 5.0E+04 | 4.95 |
| 300 | 0.0E+00 | 9.45 |

The increase in kill rate over a lengthened period of time indicates that a portion of the BTC is binding to the SK-M.

Example IV

Dispersions were prepared using suspended laponite clay loaded with benzethonium chloride. Two different suspensions were tested to determine ratios of benzethonium chloride bound (B) to the clay relative to free (F) benzethonium chloride in the suspension and tested against *Staphylococcus aureus* at different starting colony forming units (CFU) concentrations.

In a first tube, a 1:1 dilution of each sample was prepared by diluting 5.0 mL of test substance in 5.0 mL distilled water. Tube 1 sat in a water bath to allow dispersal at 50° C. followed by vortexing until homogeneous. Each diluted sample received a 0.5 mL inoculum at time zero and 0.5 mL of inoculated test substance was neutralized an 10 mL of neutralizer in a second tube. 0.1 mL of a sample from tube 2 was enumerated at the contact times on plates after incubation.

The results are shown in Table 7.

TABLE 7

| Sample # | % Bound/% Free | Contact Time Secs | CFU/ml | $Log_{10}$ reduction |
|---|---|---|---|---|
| 1. | 0.2B/0.3F | 0 | 2.07E+09 | |
| | | 15 | 9.48E+06 | 2.3 |
| | | 30 | 1.22E+05 | 4.2 |
| | | 60 | 3.30E+03 | 5.8 |
| | | 0 | 1.8E+08 | |
| | | 15 | 1.65E+04 | 4.04 |
| | | 30 | 0.00E+00 | 8.26 |
| | | 60 | 0.00E+00 | 8.26 |
| 2. | 0.25B/0.25F | 0 | 2.07+09 | |
| | | 15 | 2.62E+07 | 1.9 |
| | | 30 | 4.41E+05 | 3.7 |
| | | 60 | 8.82E+3 | 5.4 |
| | | 0 | 1.80E+08 | |
| | | 15 | 3.97E+04 | 3.66 |
| | | 30 | 00.0E+00 | 8.26 |
| | | 60 | 00.0E+00 | 8.26 |

The results show that having 0.3% free benzethonium chloride is slightly more effective than having 0.25% free benzethonium chloride at high concentrations of the challenge *S. aureus* but is no more effective at *S. aureus* concentrations of about 1.80E+08.

Example V

Figure 3:
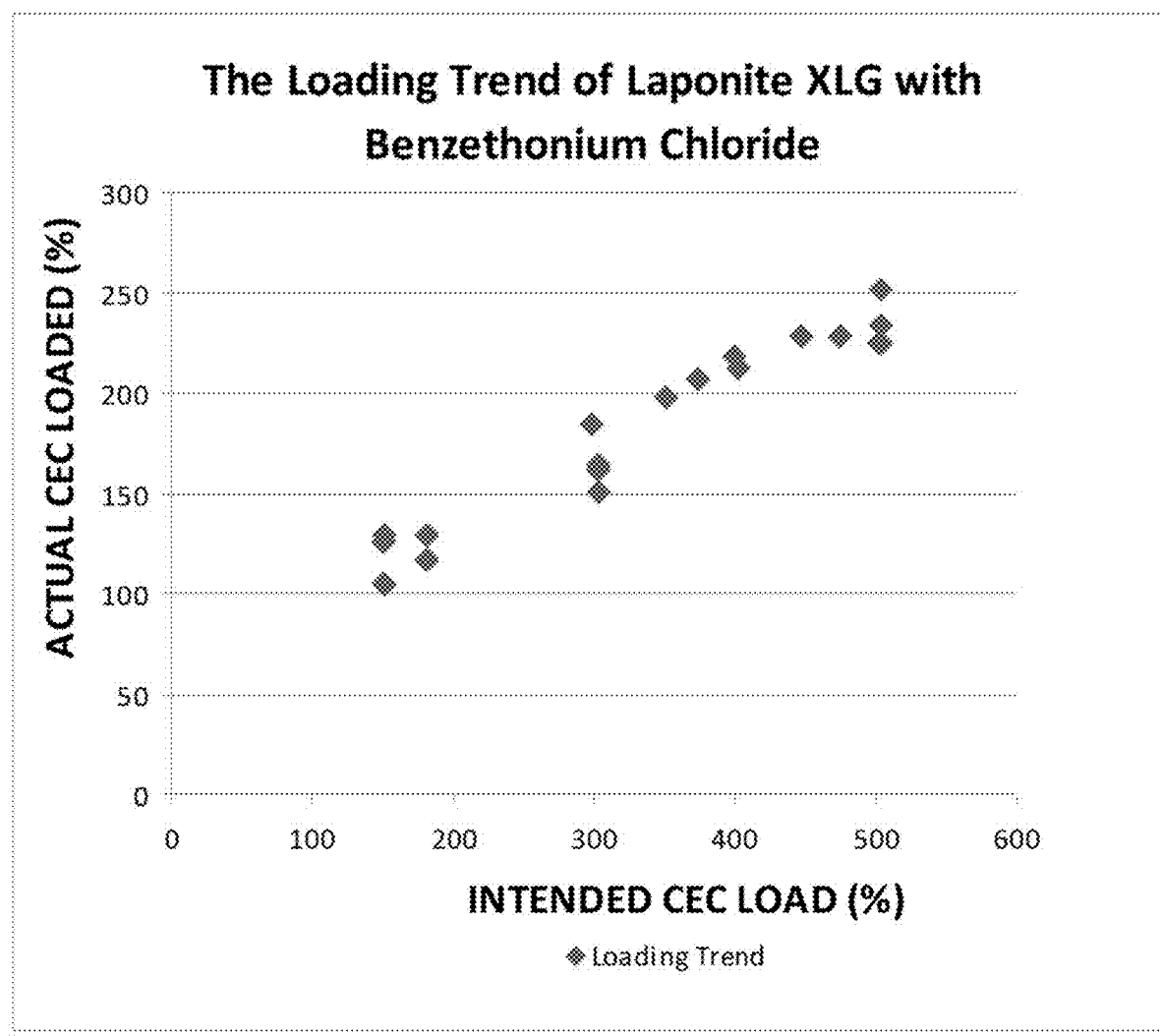
FIG. 3 is a graph showing percent binding of quaternary compound to LAPONITE clay available binding sites relative to amount of quaternary compound provided.

Hydrophilic laponite clay particulate substrate was dry mixed with benzethonium chloride quaternary ammonium antimicrobial, hydrated and allowed to set for either 30 minutes or overnight, washed and centrifuged between washings. The percentage of loading of benzethonium chloride onto the clay relative to available clay binding sites was determined for washed clay by analytical ashing. Results are shown in Table 8 and in FIG. 3.

From the data, it is apparent that loadings as high as 250% of theoretical can be obtained which is apparently due to the creation of at least secondary and tertiary layers.

TABLE 8

| Sample Number | Binding Time-min. | Wash Number | Intended CEC Load | Actual Load |
|---|---|---|---|---|
| 1 | 30 | 1 | 151 | 129 |
| | | 2 | 151 | 126 |
| | | 3 | 151 | 105 |
| 2 | 30 | 1 | 303 | 162 |
| | | 2 | 303 | 164 |
| | | 3 | 303 | 151 |
| 3 | overnight | 1 | 503 | 252 |
| | | 2 | 503 | 234 |
| | | 3 | 503 | 225 |
| 4 | overnight | 2 | 182 | 129 |
| | | 3 | 182 | 117 |
| 5 | overnight | 2 | 400 | 218 |
| 6 | overnight | 2 | 448 | 228 |
| 7 | overnight | 2 | 475 | 228 |
| 8 | overnight | 2 | 502 | 225 |
| 9 | 30 | 2 | 299 | 184 |
| 10 | 30 | 2 | 351 | 198 |
| 11 | 30 | 2 | 374 | 207 |
| 12 | 30 | 2 | 402 | 212 |

Example VI

Hydrophilic laponite clay particulate substrate was dry mixed with benzethonium chloride quaternary ammonium antimicrobial, hydrated and allowed to set for binding and washed three time and centrifuged between washings to obtain a Laponite/BTC suspension. The amount of benzethonium chloride used was enough to obtain a percentage of loading just over 100 percent of binding sites on the clay. Subsequent to addition and binding of benzethonium chloride a second compound was introduced for binding. The percentage of loading of benzethonium chloride onto the clay and binding of the second compound relative to available clay binding sites (cation exchange capacity, CEC) was determined for washed clay by analytical ashing. The second compound was added to the Laponite/BTC slurry in ethanol for binding and then washed with ethanol.

Although the present invention is not limited to any particular mechanism of action and an understanding of the mechanism of action is not necessary to practice the present invention, it is believed that the benzethonium chloride forms an intermediate secondary layer including a plurality of molecules having an ionic moiety ($N^+$ ion on the benzethonium chloride) attracted to at least one of the binding sites on the clay and the hydrophobic structure on the second compound is attracted to the hydrophobic group on the benzethonium chloride to form a tertiary layer.

Details of preparations are as follows:

1. A. Primary Load:
　　 i) Starting material
　　　　 benzethonium chloride (BTC)　　5.1 grams
　　　　 laponite clay　　18.0 grams
　　 ii) Ashing Data (ASTM D 5630)
　　　　 BTC　　16.5% (105.7% of CEC)
　　　　 Laponite Clay　　83.5%
　 B. Secondary Load 1, Vitamin A Palmitate
　　 i) Starting material
　　　　 Laponite/BTC from above　　25.0 grams
　　　　 Vitamin A Palmitate (Vit-A)　　2.8 grams
　　 ii) Ashing Data
　　　　 BTC　　16.5%
　　　　 Vit-A　　9.1%
　　　　 Laponite Clay　　74.4%
　　　　 Total % of CEC for BTC and Vit-A combined is 169.6%.
　 B. Secondary Load 2, N,N-Diethyl-meta-toluamide (DEET)
　　 i) Starting material
　　　　 Laponite/BTC from above　　25.0 grams
　　　　 DEET　　1.1 grams
　　 ii) Ashing Data
　　　　 BTC　　16.5%
　　　　 DEET　　1.3%
　　　　 Laponite Clay　　82.1%
　　　　 Total % of CEC for BTC and DEET combined is 116.2%.

Example VII

Figure 4:
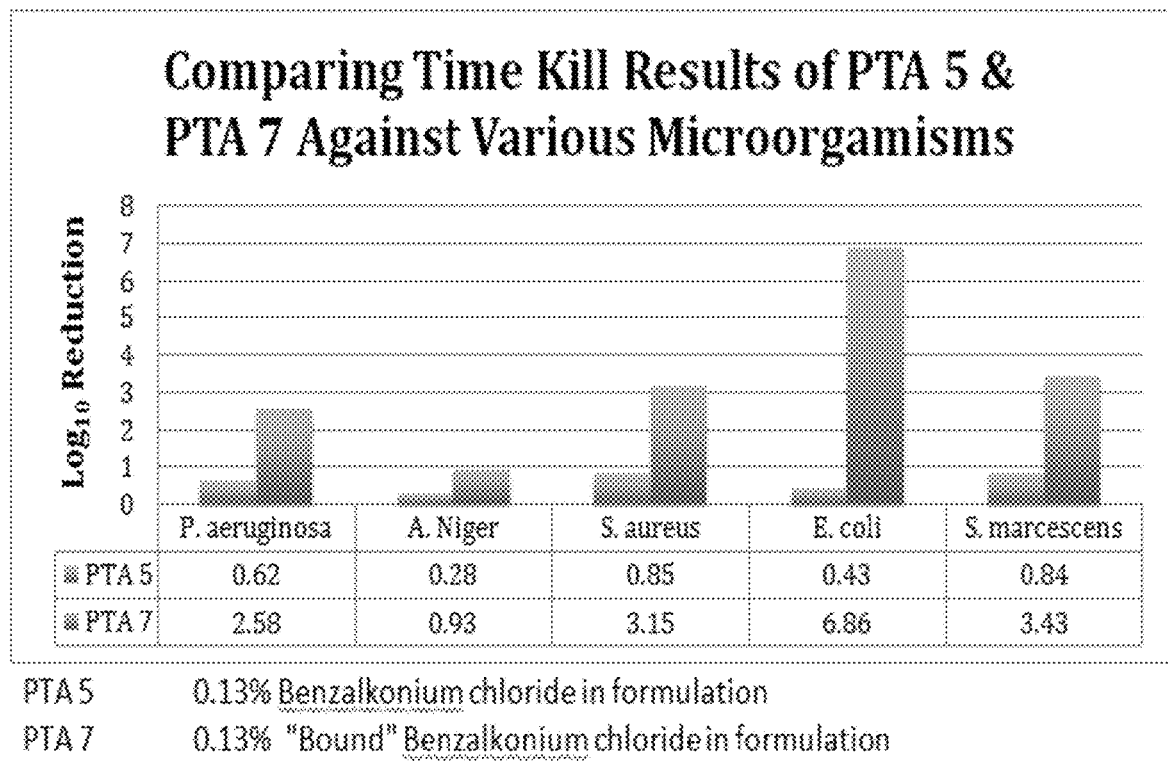
FIG. 4 shows a graph of microbial reduction by free and bound benzalkonium chloride for various microorganisms.

Experiments were conducted during development of embodiments of the present invention to assess antimicrobial activity using a time-kill procedure. The test material or a dilution of the test material was exposed to a known population of microorganism for a desired period of time. The activity of the test material was assessed by removing an aliquot of test material/microorganism mixture at a specified sampling interval (e.g., 30 seconds) and neutralizing the activity with an appropriate neutralizer (Dey Engley Neutralizing Broth) technique. Any surviving microorganisms in the neutralized test material were then enumerated. The percent or $log_{10}$ reduction, or both, was calculated from either an initial microbial population or a test blank. For all microorganisms tested, the formulation with the Benzalkonium chloride modified by the technology described herein (PTA 7) out-performed the formulation with the free Benzalkonium chloride (PTA 5) (SEE FIG. 4).

Example VIII

Figure 5:
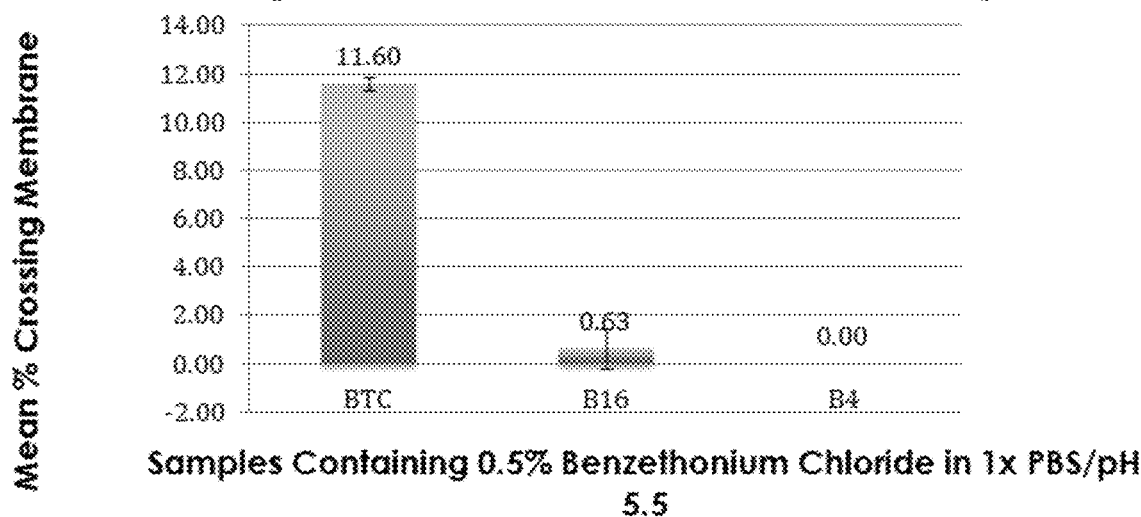
FIG. 5 shows a graph of absorption of various benzethonium chloride compositions across a membrane.

Experiments were conducted during development of embodiments of the present invention to measure the permeability of Benzethonium Chloride (Lonza, Gonzalez, Tex.) across a polyester membrane Transwell-Clear Inserts on a 24-well plate (Corning), each a diameter of 0.33 $cm^2$. Each sample was prepared with 1×PBS at pH 5.5 to a concentration of 0.5% Benzethonium Chloride. After each well was pretreated with 35 ul of 5% hexadecane/95% hexane, it was allowed to dry for one hour in a fume hood to insure evaporation of hexane. 100 ul of each fluid was delivered to the pretreated wells. Controls of 1×PBS at pH 5.5 were also delivered to wells. A lid and plastic wrap was used to prevent evaporation of the plate and incubated for 5 hours at room temperature under constant light shaking (50-100 rpm). The receiver fluid was then transferred to a 4 ml vial and processed. This includes adding 1.2 ml of ethyl acetate to each vial, mixing well with vortexing and sonication. After centrifuging at 3000× rpm for 5 minutes, the organic layer was transferred to the labeled test tube under nitrogen. Before running sample in a Shimadzu GC-MS it was reconstituted with 0.5 ml of methanol. Results demonstrate reduced absorption and thus reduced toxicity for the Benzethonium chloride bioclay over Benzethonium chloride alone (See Table 9 and FIG. 5).

TABLE 9

| SAMPLE | CODE | BTC CONC. | CEC % | MEAN % | STDEV |
|---|---|---|---|---|---|
| Benzethonium Chloride | BTC | 0.50% | N/A | 11.60 | 0.28 |
| Benzethonium Chloride Bioclay | B16 | 0.50% | 213.9 | 0.63 | 0.82 |
| Benzethonium Chloride Bioclay | B4 | 0.50% | 93.7 | 0.00 | 0.00 |

We claim:
1. An antimicrobial composition for application to the skin of a subject, comprising a dispersion, said dispersion comprising a dispersed phase within an aqueous phase comprising deionized water, said composition comprising:
   a layered hydrous magnesium silicate having binding sites in said dispersed phase; and
   a quaternary ammonium compound in said dispersed phase;
wherein said quaternary ammonium compound is loaded into said layered hydrous magnesium silicate clay with a percentage loading relative to available layered hydrous magnesium silicate clay binding sites of greater than 200%; and
wherein said dispersion is made by the method of i) dry mixing said layered hydrous magnesium silicate clay and said quaternary ammonium compound to produce a mixture; ii) adding water to said mixture to form a suspension; and iii) incubating said suspension in said water to form said dispersion.

2. The composition of claim 1, wherein said composition is selected from the group consisting of creams, lotions, gels, ointments, and liquids.

3. The composition of claim 1, wherein said quaternary ammonium compound is benzethonium chloride.

4. The composition of claim 1, wherein said aqueous phase comprises deionized water.

5. The composition of claim 1, wherein an emulsifier is added to said suspension.

6. The composition of claim 1, wherein said emulsifier is emulsifying wax.

7. The composition of claim 1, further comprising a humectant in said aqueous phase.

8. The composition of claim 7, wherein said humectant is selected from the group consisting of glycerol, propylene glycol, and liquid silicone.

9. The composition of claim 1, further comprising polydimethylsiloxane.

10. The composition of claim 1, further comprising an emollient, detackifier, moisturizer, thickener, or chelating agent.

11. The composition of claim 1, wherein said composition further comprises an additional agent.

12. The composition of claim 11, wherein said additional agent is selected from the group consisting of an antimicrobial agent, an analgesic, an anti-fungal agent, and an anti-inflammatory agent.

* * * * *